United States Patent
Sakimoto

(10) Patent No.: US 11,006,918 B2
(45) Date of Patent: May 18, 2021

(54) TOMOGRAPHIC IMAGE GENERATION METHOD AND RADIOGRAPHIC IMAGING APPARATUS

(71) Applicant: Shimadzu Corporation, Kyoto (JP)

(72) Inventor: Tomonori Sakimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 32 days.

(21) Appl. No.: 16/612,960

(22) PCT Filed: Mar. 12, 2018

(86) PCT No.: PCT/JP2018/009490
§ 371 (c)(1),
(2) Date: Nov. 12, 2019

(87) PCT Pub. No.: WO2019/003506
PCT Pub. Date: Jan. 3, 2019

(65) Prior Publication Data
US 2020/0170606 A1    Jun. 4, 2020

(30) Foreign Application Priority Data

Jun. 30, 2017 (JP) .............................. JP2017-128353

(51) Int. Cl.
| | |
|---|---|
| G06T 7/00 | (2017.01) |
| A61B 6/00 | (2006.01) |
| A61B 6/02 | (2006.01) |
| G06T 11/00 | (2006.01) |
| A61B 6/03 | (2006.01) |

(52) U.S. Cl.
CPC ............ *A61B 6/5258* (2013.01); *A61B 6/025* (2013.01); *A61B 6/032* (2013.01); *G06T 11/005* (2013.01)

(58) Field of Classification Search
CPC ... G06T 7/0012; G06T 11/003; G06T 11/005; G06T 2207/10081; A61B 6/5252; A61B 5/602; A61B 6/025; A61B 6/463; A61B 6/481; A61B 6/03; A61B 6/5258; A61B 6/032
See application file for complete search history.

(56) References Cited

U.S. PATENT DOCUMENTS

2017/0236276 A1* 8/2017 Fukuda ................. A61B 6/025
                                                            382/131

FOREIGN PATENT DOCUMENTS

JP         2016-127870 A      7/2016

OTHER PUBLICATIONS

Machida et al., "Optimizing Parameters for Flat-Panel Detector Digital Tomosynthesis," RadioGraphics 2010; 30:549-562 (2010).
Written Opinion dated Jun. 5, 2018 by the International Search Authority for PCT application PCT/JP2018/009490, submitted with a partial machine translation.

* cited by examiner

*Primary Examiner* — Don K Wong
(74) *Attorney, Agent, or Firm* — Muir Patent Law, PLLC

(57) ABSTRACT

A tomographic image generation method includes acquiring a first tomographic image (T1) including microstructure information (M) and a first ripple artifact (R1), acquiring a second tomographic image (T2) including a second ripple artifact (R2), and acquiring a subtraction tomographic image (T3) by subtracting the second tomographic image from the first tomographic image.

8 Claims, 8 Drawing Sheets

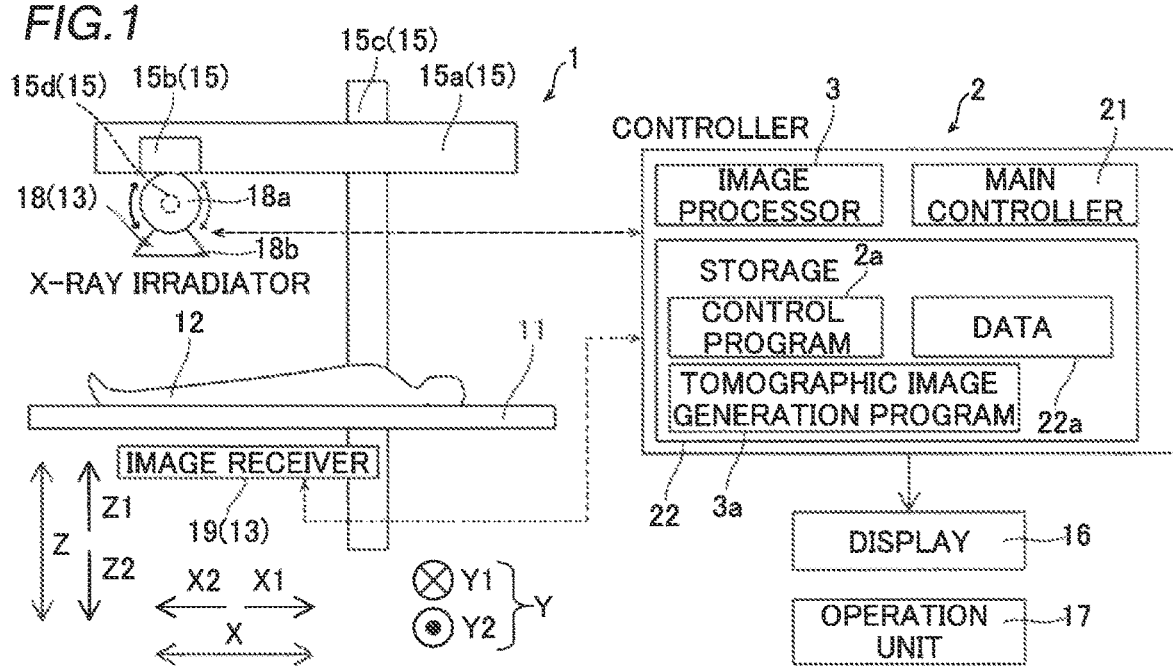
FIG.1
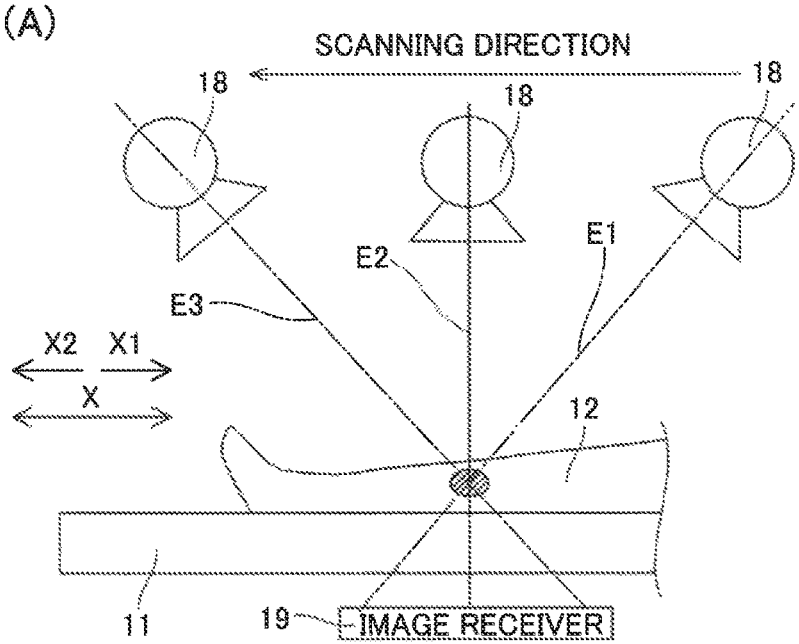
FIG.2 (A)
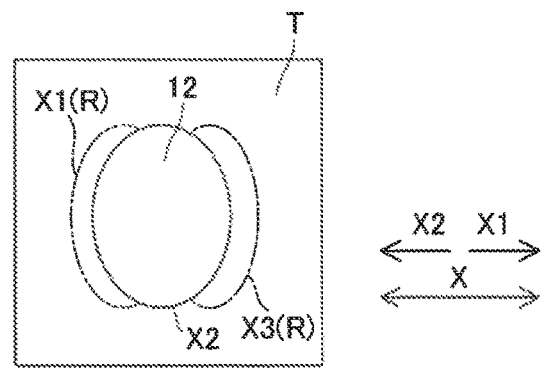
(B)

(B)

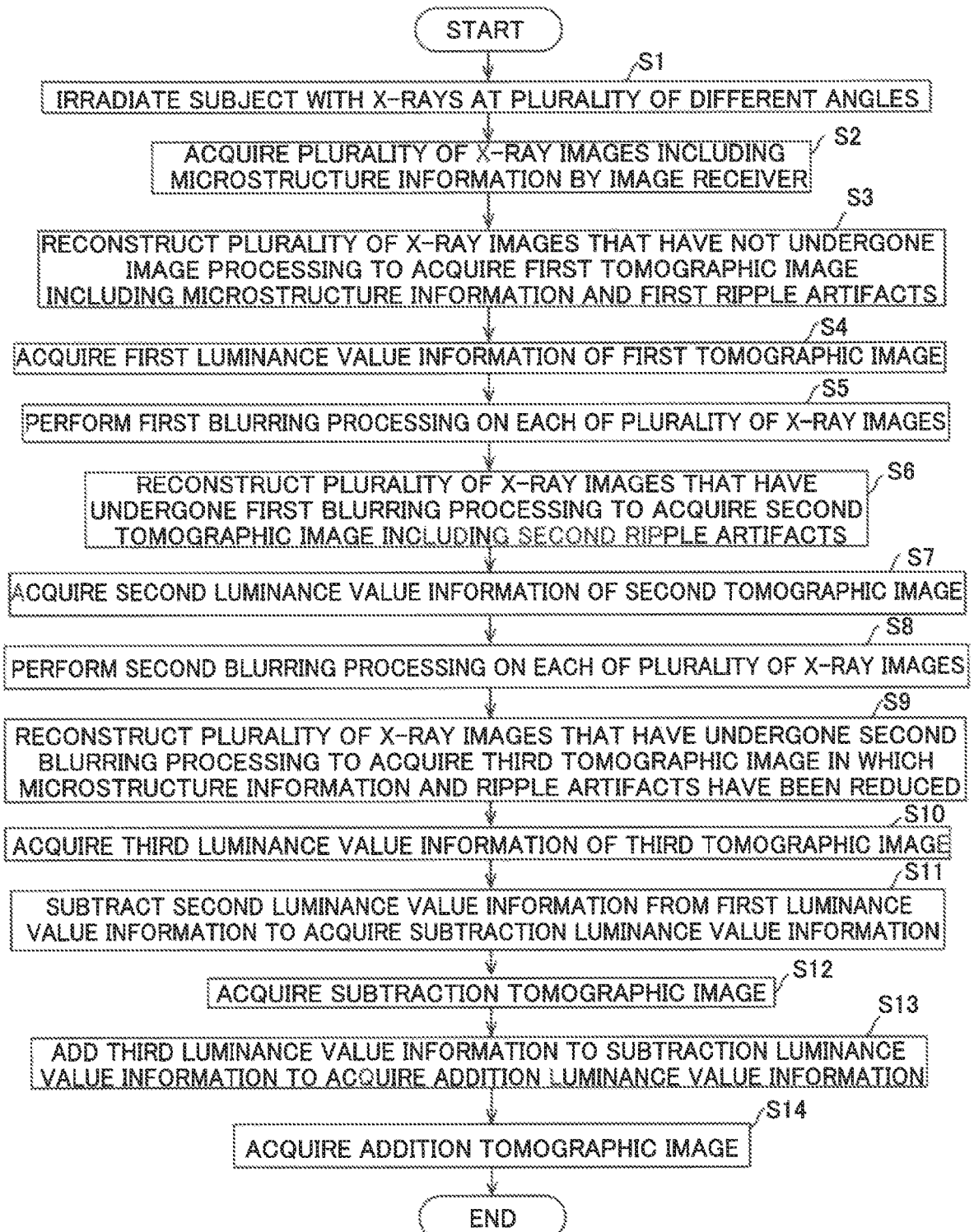

TOMOGRAPHIC IMAGE GENERATION METHOD AND RADIOGRAPHIC IMAGING APPARATUS

TECHNICAL FIELD

The present invention relates to a tomographic image generation method and a radiographic imaging apparatus, and more particularly, it relates to a tomographic image generation method and a radiographic imaging apparatus for acquiring a tomographic image based on a projection image acquired by irradiating a subject with X-rays.

BACKGROUND ART

Conventionally, an X-ray fluoroscope that acquires a tomosynthesis image (tomographic image) based on a fluoroscopic image (projection image) acquired by irradiating an object (subject) with X-rays (radiation) is known. Such an X-ray fluoroscope is disclosed in Japanese Patent Laid-Open No. 2016-127870, for example. A tomosynthesis image refers to a tomographic image at an arbitrary height obtained by reconstructing projection images of an object imaged from different angles.

The X-ray fluoroscope disclosed in Japanese Patent Laid-Open No. 2016-127870 includes an X-ray source that irradiates an object with X-rays, a detector that detects the X-rays, and a controller that acquires projection images by converting the X-rays detected by the detector into electrical signals in accordance with the intensity. The controller is configured to pre-process the acquired projection images and generate a tomosynthesis image using a predetermined number of pre-processed projection images.

The controller of the X-ray fluoroscope disclosed in Japanese Patent Laid-Open 2016-127870 is configured to perform pre-processing on a fluoroscopic image to reduce noise. Specifically, in the pre-processing, the controller discerns a structural region from other regions for each of a predetermined number of fluoroscopic images. More specifically, the controller performs differential processing on the predetermined number of acquired fluoroscopic images, and discerns a region in which a difference value is larger than a threshold as a structural region. The controller is configured to perform no processing on the structural region and perform smoothing processing only on the other regions in the pre-processing.

PRIOR ART

Patent Document
Patent Document 1: Japanese Patent Laid-Open 2016-127870

SUMMARY OF THE INVENTION

Problems to be Solved by the Invention

The controller of the X-ray fluoroscope disclosed in Japanese Patent Laid-Open 2016-127870 discerns the region in which the difference value is larger than the threshold as the structural region in the pre-processing. Thus, in the controller, because of a small number of fluoroscopic images, the influence of artifacts due to high-contrast regions is increased, and it may be difficult to discern the structural region. Furthermore, the controller performs no processing on the structural region, and thus artifacts due to high-contrast regions conceivably occur in the structural region of the tomosynthesis image. Therefore, a tomosynthesis image (tomographic image) in which a reduction in the image quality is significantly reduced or prevented cannot be reliably acquired even with a small number of fluoroscopic images (projection images).

The present invention is intended to solve the above problems. The present invention aims to provide a tomographic image generation method and a radiographic imaging apparatus that reliably enable acquisition of a tomographic image in which a reduction in the image quality caused by artifacts due to high-contrast regions is significantly reduced or prevented even with a small number of projection images.

Means for Solving the Problems

In order to attain the aforementioned object, a tomographic image generation method according to a first aspect of the present invention includes acquiring a plurality of projection images including microstructure information by irradiating a subject with radiation at a plurality of different angles and detecting the radiation transmitted through the subject, acquiring a first tomographic image including the microstructure information and first artifact information by directly reconstructing the plurality of projection images, performing first blurring processing on each of the plurality of projection images to maintain a high-contrast region and blur a region other than the high-contrast region, acquiring a second tomographic image including second artifact information by reconstructing the plurality of projection images that have undergone the first blurring processing, and acquiring a subtraction tomographic image by subtracting the second tomographic image from the first tomographic image.

As described above, the tomographic image generation method according to the first aspect of the present invention includes acquiring the first tomographic image including the microstructure information and the first artifact information and the second tomographic image including the second artifact information based on the plurality of projection images and acquiring the subtraction tomographic image by subtracting the second tomographic image from the first tomographic image. In the second tomographic image, the second artifact information due to the high-contrast region is acquired by blurring the region other than the high-contrast region. Thus, the second artifact information of the second tomographic image is subtracted from the first artifact information of the first tomographic image such that the artifact information due to the high-contrast region can be reduced in the subtraction tomographic image. Consequently, it is possible to obtain the tomographic image generation method that reliably enables acquisition of the subtraction tomographic image in which a reduction in the image quality caused by the artifact due to the high-contrast region is significantly reduced or prevented even with a small number of projection images.

In the aforementioned tomographic image generation method according to the first aspect, the second tomographic image is preferably subtracted from the first tomographic image to acquire the subtraction tomographic image including a difference between the first artifact information and the second artifact information and the microstructure information. Accordingly, the first artifact information, which is unnecessary information, is reduced by the second artifact information, and thus it is possible to obtain the tomographic image generation method that enables acquisition of the subtraction tomographic image in which a reduction in the image quality caused by the artifact due to the high-contrast region is significantly reduced or prevented and necessary information remains.

In this case, each of the plurality of projection images preferably undergoes second blurring processing to apply blurring throughout the projection image, the plurality of projection images that have undergone the second blurring processing are preferably reconstructed to acquire a third tomographic image, and the third tomographic image is preferably added to the subtraction tomographic image to acquire an addition tomographic image. In the subtraction tomographic image, the microstructure information remains, and information of the region other than the high-contrast region is reduced. On the other hand, the third tomographic image has the information of the region other than the high-contrast region. Therefore, it is possible to obtain the tomographic image generation method that enables acquisition of the addition tomographic image, in which only the artifact information has been reduced, including the information of the region other than the high-contrast region by adding the subtraction tomographic image and the third tomographic image.

In the aforementioned tomographic image generation method including the first tomographic image, the second tomographic image, and the third tomographic image, the addition tomographic image is preferably acquired by subtracting second luminance value information included in the second tomographic image from first luminance value information included in the first tomographic image and adding third luminance value information included in the third tomographic image. Accordingly, the addition tomographic image can be acquired by calculating only the luminance value information of each of the first tomographic image, the second tomographic image, and the third tomographic image, and thus it is possible to obtain the tomographic image generation method that enables acquisition of the addition tomographic image by a simple method.

In the aforementioned tomographic image generation method according to the first aspect, in the first blurring processing, a region having a higher contrast than the microstructure information is preferably maintained as the high-contrast region, and a region other than the region having the higher contrast than the microstructure information is preferably blurred. Accordingly, the microstructure information can be reliably reduced by the first blurring processing, and thus it is possible to obtain the tomographic image generation method capable of significantly reducing or preventing a reduction in the microstructure information when the second tomographic image is subtracted from the first tomographic image to acquire the subtraction tomographic image.

A radiographic imaging apparatus according to a second aspect of the present invention includes an imager configured to irradiate a subject with radiation at a plurality of different angles, to detect the radiation transmitted through the subject, and to capture a plurality of projection images including microstructure information, and an image processor configured to process the plurality of projection images captured by the imager. The image processor is configured to acquire a first tomographic image including the microstructure information and first artifact information by directly reconstructing the plurality of projection images, to perform first blurring processing on each of the plurality of projection images so as to maintain a high-contrast region and blur a region other than the high-contrast region, to acquire a second tomographic image including second artifact information by reconstructing the plurality of projection images that have undergone the first blurring processing, and to acquire a subtraction tomographic image by subtracting the second tomographic image from the first tomographic image.

In the radiographic imaging apparatus according to the second aspect of the present invention, as described above, the image processor is configured to acquire the first tomographic image including the microstructure information and the first artifact information and the second tomographic image including the second artifact information based on the plurality of projection images and to acquire the subtraction tomographic image by subtracting the second tomographic image from the first tomographic image. In the second tomographic image, the second artifact information due to the high-contrast region is acquired by blurring the region other than the high-contrast region. Thus, the second artifact information of the second tomographic image is subtracted from the first artifact information of the first tomographic image such that the artifact information due to the high-contrast region can be reduced in the subtraction tomographic image. Consequently, even with a small number of projection images, it is possible to reliably acquire the subtraction tomographic image in which a reduction in the image quality caused by the artifact due to the high-contrast region is significantly reduced or prevented.

In the aforementioned radiographic imaging apparatus according to the second aspect, the subtraction tomographic image preferably includes a difference between the first artifact information and the second artifact information and the microstructure information. Accordingly, the first artifact information, which is unnecessary information, is reduced by the second artifact information while the microstructure information, which is necessary information, remains, and thus the subtraction tomographic image in which a reduction in the image quality caused by the artifact due to the high-contrast region is significantly reduced or prevented and the necessary information remains can be acquired.

In this case, the image processor is preferably configured to perform second blurring processing on each of the plurality of projection images so as to apply blurring throughout the projection image, to acquire a third tomographic image by reconstructing the plurality of projection images that have undergone the second blurring processing, and to acquire an addition tomographic image by adding the third tomographic image to the subtraction tomographic image. In the subtraction tomographic image, the microstructure information remains, and information of the region other than the high-contrast region is reduced. On the other hand, the third tomographic image has only the information of the region other than the high-contrast region. Therefore, the subtraction tomographic image and the third tomographic image are added such that the addition tomographic image, in which only the artifact information has been reduced, including the necessary information can be acquired.

Effect of the Invention

According to the present invention, as described above, it is possible to reliably acquire the tomographic image in which a reduction in the image quality caused by the artifact due to the high-contrast region is significantly reduced or prevented even with a small number of projection images.

BRIEF DESCRIPTION OF THE DRAWINGS

FIG. 1 is a schematic view showing the overall configuration of an X-ray imaging apparatus according to an embodiment of the present invention.

FIG. 2(A) is a schematic side view showing a state in which the X-ray imaging apparatus images the knee joint by triple irradiation, and FIG. 2(B) is a schematic front view showing a tomographic image obtained by reconstructing the X-ray images captured in FIG. 2(A).

FIG. 9 is a flowchart showing tomographic image generation processing of the X-ray imaging apparatus according to the embodiment of the present invention.

MODES FOR CARRYING OUT THE INVENTION

Figure 3:
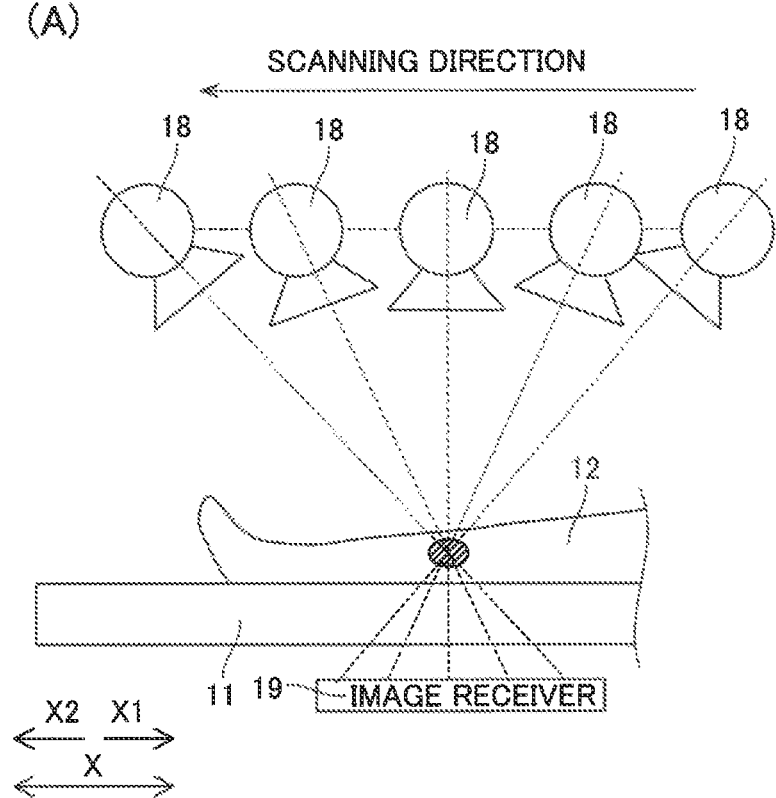
FIG. 3(A) is a schematic side view showing a state in which the X-ray imaging apparatus images the knee joint by multiple irradiation.
FIG. 3(B) is a schematic front view showing a tomographic image obtained by reconstructing the X-ray images captured in FIG. 3(A).
Figure 3:
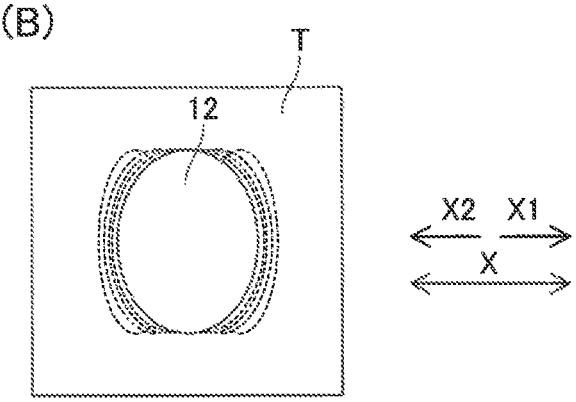

An embodiment embodying the present invention is hereinafter described on the basis of the drawings.

This Embodiment

The configuration of an X-ray imaging apparatus 1 according to this embodiment is now described with reference to FIGS. 1 to 9. The X-ray imaging apparatus 1 is an example of a "radiographic imaging apparatus" in the claims.

As shown in FIG. 1, the X-ray imaging apparatus 1 is configured to irradiate a subject 12 lying on an imaging table 11 with X-rays and detect the X-rays transmitted through the subject 12 so as to image the subject 12. The X-rays are examples of "radiation" in the claims.

Specifically, the X-ray imaging apparatus 1 includes an imager 13, the imaging table 11, an irradiator moving mechanism 15, a controller 2, a display 16, and an operation unit 17. The imager 13 is configured to irradiate the subject 12 with X-rays at a plurality of different angles and detect the X-rays transmitted through the subject 12 so as to capture a plurality of X-ray images. Specifically, the imager 13 includes an X-ray irradiator 18 and an image receiver 19.

In the X-ray imaging apparatus 1, the X-rays radiated from the X-ray irradiator 18 disposed above the imaging table 11 and transmitted through the subject 12 are received by the image receiver 19, and X-ray images are captured. This X-ray imaging apparatus 1 is an example of a so-called island-type X-ray imaging apparatus 1. The X-ray images are examples of a "projection image" in the claims. The length direction of the imaging table 11 is defined as an X direction. In the X direction, a direction toward one side is defined as an X1 direction, and a direction toward the other side is defined as an X2 direction. A direction perpendicular to the X direction in a horizontal direction is defined as a Y direction. In the Y direction, a direction toward one side is defined as a Y1 direction, and a direction toward the other side is defined as a Y2 direction. A direction perpendicular to the X direction and the Y direction is defined as a Z direction (upward-downward direction). In the Z direction, a direction toward one side is defined as a Z1 direction, and a direction toward the other side is defined as a Z2 direction.

The X-ray irradiator 18 includes an X-ray tube 18a that generates X-rays and a collimator 18b that limits an X-ray irradiation range by shielding the X-rays. The irradiator moving mechanism 15 includes a first guide mechanism 15a that moves the X-ray irradiator 18 in the X direction, a second guide mechanism 15b that moves the X-ray irradiator 18 in the Y direction, and a third guide mechanism 15c that moves the first guide mechanism 15a in the Z direction. The first guide mechanism 15a includes a rotating mechanism 15d that rotates the X-ray irradiator 18 about a rotation axis. The irradiator moving mechanism 15 is automatically controlled by the controller 2.

The image receiver 19 receives the X-rays radiated by the X-ray irradiator 18 and transmitted through the subject 12, and converts the received X-rays into electrical signals. The image receiver 19 is an X-ray detector such as a flat panel detector (FPD). The image receiver 19 is electrically connected to the controller 2, and X-ray information (detection signals) converted into electrical signals is transmitted to the controller 2. On the flat upper surface of the imaging table 11, the subject 12 is placed in a recumbent state (recumbent position) in which the body axis extends along the X direction.

The controller 2 is an information processor such as a personal computer (PC), and mainly includes a main controller 21 such as a central processing unit (CPU), a storage 22 such as a hard disc drive (HDD) and a memory, and an image processor 3. The main controller 21 is configured to control X-ray irradiation of the X-ray irradiator 18 and control detection signal readout of the image receiver 19. Specifically, the main controller 21 controls the X-ray imaging apparatus 1 by executing a control program 2a stored in the storage 22. The image processor 3 is configured to process a plurality of X-ray images captured by the imager 13. The image processor 3 processes the detection signals (electrical signals) acquired from the image receiver 19 to generate X-ray images. The image processor 3 generates a tomographic image T (tomosynthesis image) from the X-ray images by executing a tomographic image generation program 3a stored in the storage 22. The image processor 3 is described in detail below. The storage 22 stores various types of data 22a including captured X-ray images.

The display 16 is an image display such as a liquid crystal monitor, and performs screen display based on the image output of the controller 2. The operation unit 17 includes a keyboard, a mouse, an operation lever, etc. that receive user operation inputs. The controller 2 is configured to receive a mode selection of an imaging mode, inputs of various imaging conditions, and an instruction to start imaging via the operation unit 17.

<Image Processor>

The image processor 3 is configured to acquire a tomographic image T based on a plurality of X-ray images. As an example, as shown in FIG. 2(A), the subject 12 (knee joint) is irradiated with X-rays at a plurality of (three) different angles, and the image receiver 19 detects the X-rays transmitted through the subject 12 such that the image processor 3 acquires a plurality of (three) X-ray images. The X-ray irradiator 18 irradiates the subject 12 with X-rays in order of a first irradiation position E1, a second irradiation position E2, and a third irradiation position E3 from the head side. At this time, the X-ray irradiator 18 is moved along a scanning direction (X2 direction) by the first guide mechanism 15a, and is rotated at an appropriate angle about the rotation axis by the rotating mechanism 15d at the irradiation position.

Then, the image processor 3 acquires the tomographic image T by reconstructing (such as a shift addition method) the plurality of (three) acquired X-ray images. The X-ray image of the subject 12 acquired at the first irradiation position E1 is taken as a first X-ray image X1, the X-ray image of the subject 12 acquired at the second irradiation position E2 is taken as a second X-ray image X2, and the X-ray image of the subject 12 acquired at the third irradiation position E3 is taken as a third X-ray image X3. However, the positions of the X-ray images of the subject 12 detected by the image receiver 19 are different from each other, and thus as shown in FIG. 2(B), in the acquired tomographic image T, the X-ray images appear as ripple artifacts R. That is, the first X-ray image X1 and the third X-ray image X3 appear at positions deviated from the second X-ray image X2 in the tomographic image T. The ripple artifacts R are virtual images of the subject 12 generated at positions deviated in the tomographic image T. The ripple artifacts R are artifacts generated due to high-contrast regions HC, which are portions of the X-ray images with a large difference in luminance value. Therefore, the ripple artifacts themselves each have a higher luminance value than other regions.

In order to prevent the ripple artifacts R shown in FIG. 2(B) from appearing in the tomographic image T, the number of irradiation positions at which the X-ray irradiator 18 irradiates the subject 12 with X-rays is conceivably increased, as shown in FIG. 3(A). Although there are five irradiation positions in FIG. 3(A) due to a space for the drawing, the number of irradiation positions may be six or more. Thus, as shown in FIG. 3(B), it is possible to blur the ripple artifacts R that have appeared in the tomographic image T. However, the number of irradiation positions is increased such that the working time for obtaining the tomographic image T of the subject 12 by the X-ray imaging apparatus 1 increases. The reading time of the image receiver 19 of the X-ray imaging apparatus 1 is reduced such that an increase in the working time of the X-ray imaging apparatus 1 is significantly reduced or prevented. However, there may be a case in which the conventional equipment cannot sufficiently reduce the reading time due to the performance of the image receiver 19, and in this case, the equipment of the X-ray imaging apparatus 1 needs to be changed. Therefore, there is a possibility that the existing equipment cannot be used in order to obtain the tomographic image T in which the ripple artifacts R have been sufficiently reduced.

Therefore, the X-ray imaging apparatus 1 according to this embodiment is configured to be able to acquire the tomographic image T in which the ripple artifacts R have been reduced without increasing the number of irradiation positions of the X-ray irradiator 18. The image processor 3 of the X-ray imaging apparatus 1 according to this embodiment is described below. On the tomographic images T in FIGS. 4 to 8, for easy viewing of the drawings, portions displayed in black on an actual tomographic image T are shown in white, and portions displayed in white on the actual tomographic image T are shown in black.

The image processor 3 is configured to read the tomographic image generation program 3a based on image reconstruction processing (image reconstruction method) from the storage 22 and execute the same, as shown in FIG. 1, in order to acquire the tomographic image T in which the ripple artifacts R have been reduced. Specifically, the image processor 3 is configured to generate a first tomographic image T1 (see FIG. 4), a second tomographic image T2 (see FIG. 5), and a third tomographic image T4 (see FIG. 7) from a plurality of X-ray images, generate a subtraction tomographic image T3 (see FIG. 6) by subtracting the second tomographic image T2 from the first tomographic image T1, and generate an addition tomographic image T5 (see FIG. 8) by adding the third tomographic image T4 to the subtraction tomographic image T3.

Figure 4:
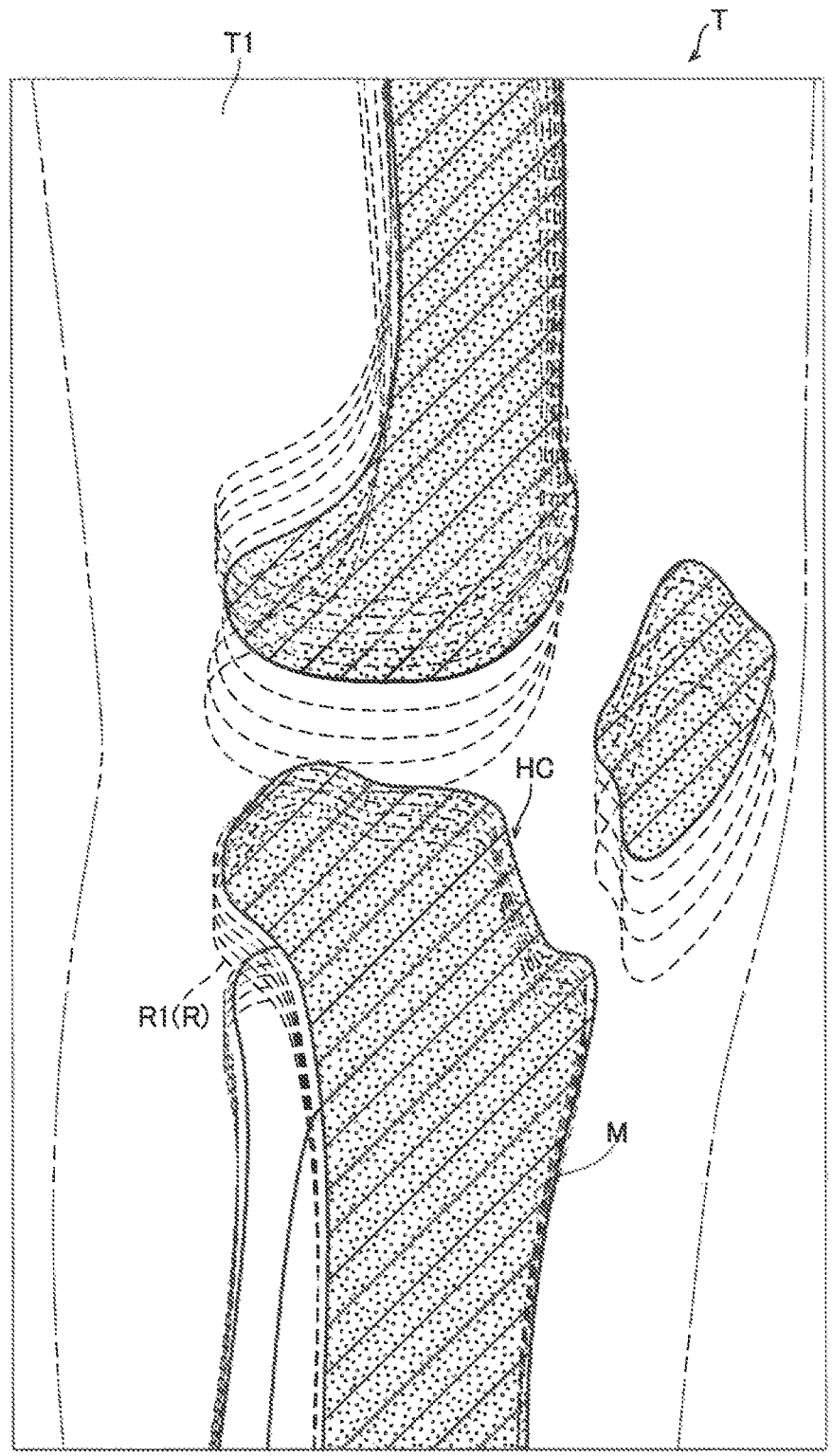
FIG. 4 is a schematic front view showing a first tomographic image including microstructure information and first ripple artifacts captured by the X-ray imaging apparatus according to the embodiment of the present invention.

The image processor 3 controls the X-ray irradiator 18 to radiate X-rays at a plurality of different angles, and acquires a plurality of X-ray images including microstructure information M. The microstructure information M is image information of a so-called trabecula of a bone tissue, for example. Then, as shown in FIG. 4, the image processor 3 acquires the first tomographic image T1 including the microstructure information M and first ripple artifacts R1 by directly reconstructing the plurality of X-ray images. At this time, the image processor 3 acquires first luminance value information included in the first tomographic image T1. The first luminance value information includes luminance value information of each of the first ripple artifacts R1 and the microstructure information M. The first ripple artifacts R1 are examples of "first artifact information" in the claims.

The image processor 3 is configured to perform first blurring processing on each of the plurality of X-ray images so as to maintain the high-contrast regions HC and blur regions other than the high-contrast regions HC. The high-contrast regions HC are portions in which a difference in luminance value between a portion that absorbs X-rays radiated from the X-ray irradiator 18 when the X-rays are transmitted through the subject 12 to appear white in the X-ray image and a portion that does not absorb the X-rays when the X-rays are transmitted through the subject 12 to appear black in the X-ray image is large. In the first blurring processing, processing is performed by a non-linear filter (a total variation minimization (TVM) filter, for example) that does not attenuate the high-contrast regions HC but attenuates regions other than the high-contrast regions HC. Specifically, in the first blurring processing, processing is performed to maintain regions each having a higher contrast than the microstructure information M as the high-contrast regions HC and blur regions other than the regions each having a higher contrast than the microstructure information M.

Figure 5:
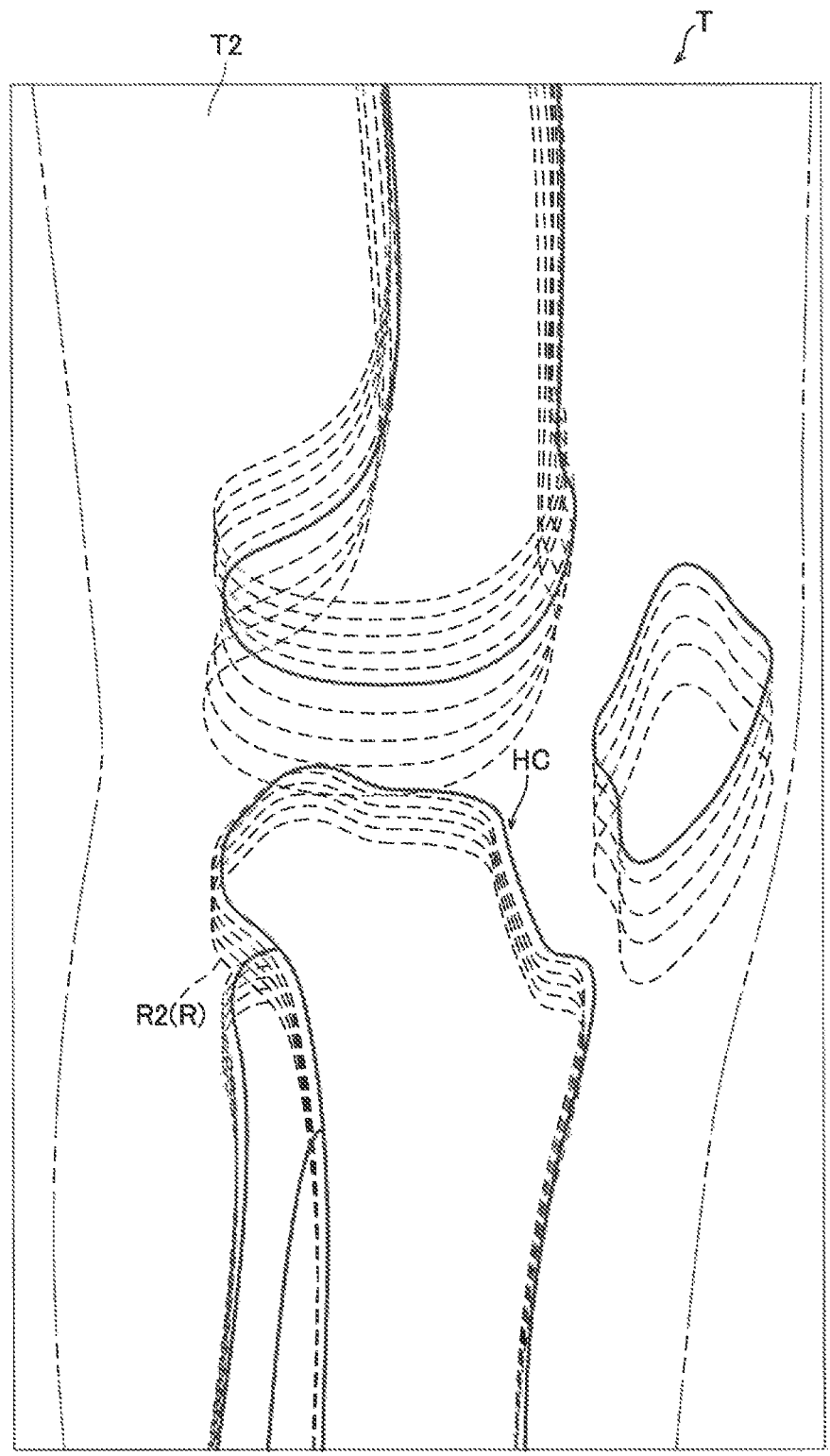
FIG. 5 is a schematic front view showing a second tomographic image including second ripple artifacts captured by the X-ray imaging apparatus according to the embodiment of the present invention.

Then, as shown in FIG. 5, the image processor 3 reconstructs the plurality of X-ray images that have undergone the first blurring processing to reduce (blur) the microstructure information M, but acquires the second tomographic image T2 including second ripple artifacts R2. At this time, the image processor 3 acquires second luminance value information included in the second tomographic image T2. The second luminance value information includes luminance value information of the second ripple artifacts R2 and the reduced microstructure information M. The second ripple artifacts R2 are examples of "second artifact information" in the claims.

Figure 6:
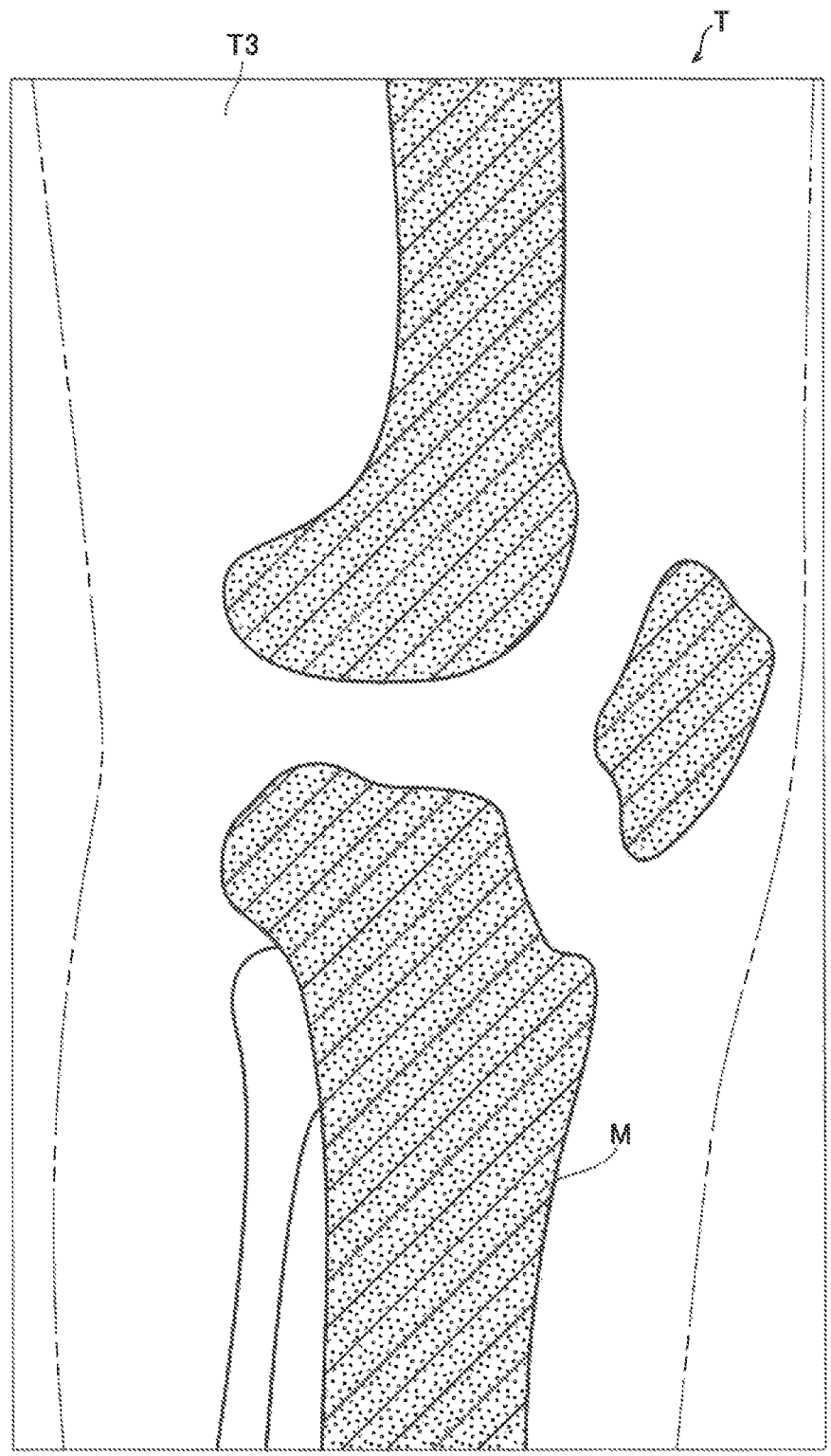
FIG. 6 is a schematic front view showing a subtraction tomographic image including microstructure information captured by the X-ray imaging apparatus according to the embodiment of the present invention.

Furthermore, as shown in FIG. 6, the image processor 3 acquires the subtraction tomographic image T3 by subtracting the second tomographic image T2 from the first tomographic image T1. That is, the image processor 3 performs processing to subtract the second luminance value information included in the second tomographic image T2 including the second ripple artifacts R2 from the first luminance value information included in the first tomographic image T1 including the microstructure information M and the first ripple artifacts R1. At this time, the image processor 3 acquires subtraction luminance value information included in the subtraction tomographic image T3. The subtraction luminance value information includes difference information between the first ripple artifacts R1 and the second ripple artifacts R2 and difference information of the microstructure information M between the first ripple artifacts R1 and the second ripple artifacts R2.

Thus, the subtraction tomographic image T3 includes the difference information between the first ripple artifacts R1 and the second ripple artifacts R2 and the difference information of the microstructure information M. The plurality of X-ray images for generating the second tomographic image T2 undergo the first blurring processing.

Therefore, the first ripple artifacts R1 of the first tomographic image T1 and the second ripple artifacts R2 of the second tomographic image T2 are substantially the same ripple artifacts R. Consequently, the difference information between the first ripple artifacts R1 and the second ripple artifacts R2 is sufficiently reduced. On the other hand, the difference information of the microstructure information M remains without being reduced so much.

Consequently, the subtraction tomographic image T3 becomes a tomographic image T in which the first ripple artifacts R1 have been reduced from the first tomographic image T1, as shown in FIG. 6. However, when the second tomographic image T2 is subtracted from the first tomographic image T1, not only information of the first ripple artifacts R1 but also contrast information of the image is subtracted. Therefore, it is difficult to say that the subtraction tomographic image T3 is a tomographic image T that sufficiently includes image information. Thus, the image processor 3 according to this embodiment is configured to add the tomographic image T including the contrast information to the subtraction tomographic image T3 (T1–T2). Specifically, the image processor 3 generates the tomographic image T including the contrast information, holding the microstructure information M, and having the reduced ripple artifacts R.

The image processor 3 is configured to perform second blurring processing on each of the plurality of X-ray images so as to apply blurring throughout the X-ray image. In the second blurring processing, processing is performed to acquire the third tomographic image T4 in which the microstructure information M and the ripple artifacts R have been reduced. Specifically, in the second blurring processing, processing is performed by a filter (an averaging filter, for example) that attenuates the entire X-ray images.

Figure 7:
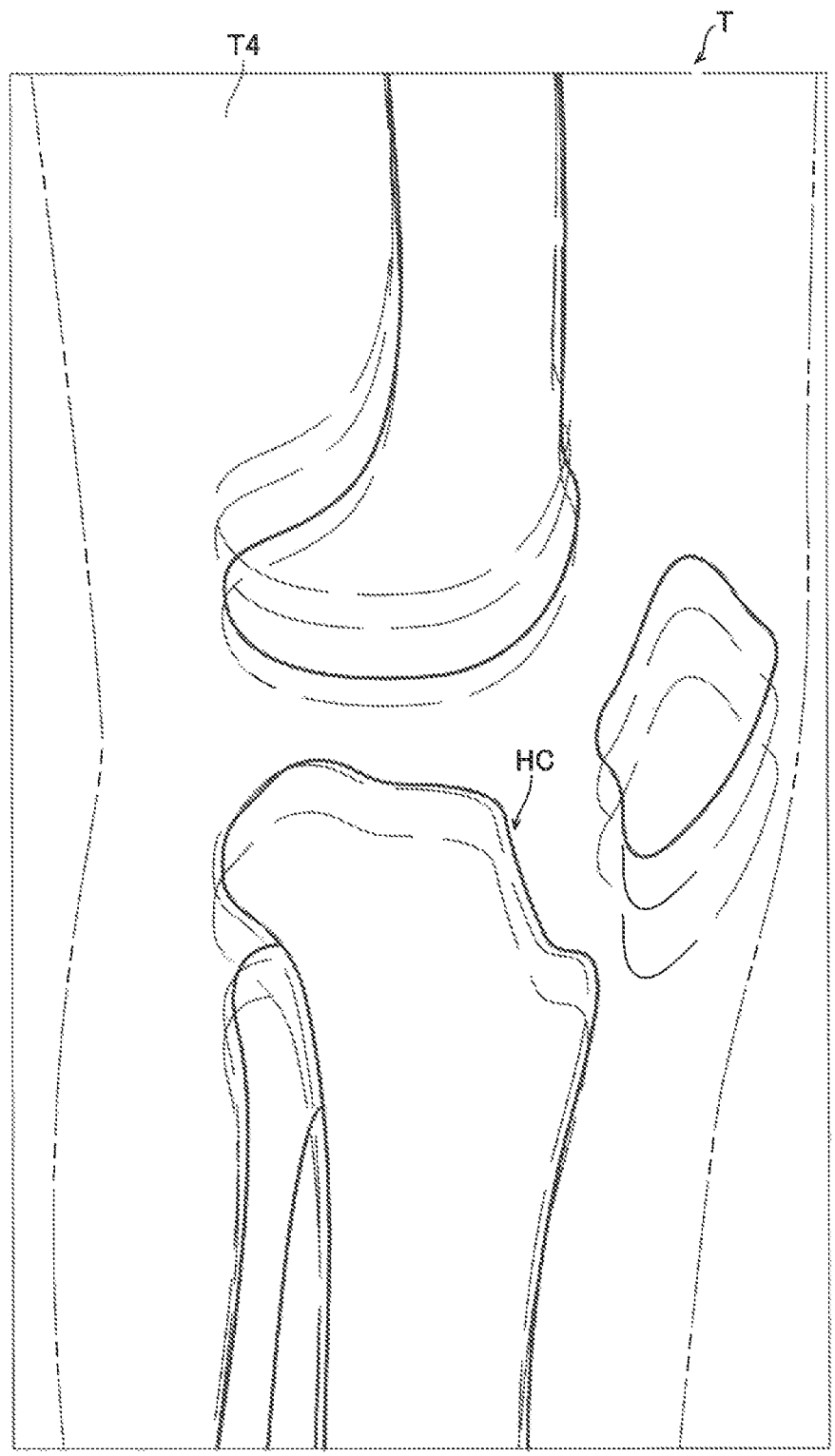
FIG. 7 is a schematic front view showing a third tomographic image captured by the X-ray imaging apparatus according to the embodiment of the present invention.

Then, as shown in FIG. 7, the image processor 3 acquires the third tomographic image T4 by reconstructing the plurality of X-ray images that have undergone the second blurring processing. At this time, the image processor 3 acquires third luminance value information included in the third tomographic image T4. The third tomographic image T4 is a tomographic image T in which the microstructure information M and the ripple artifacts R have been reduced. The third tomographic image T4 includes the luminance value information of the microstructure information M that is similar to that of the second tomographic image T2.

Figure 8:
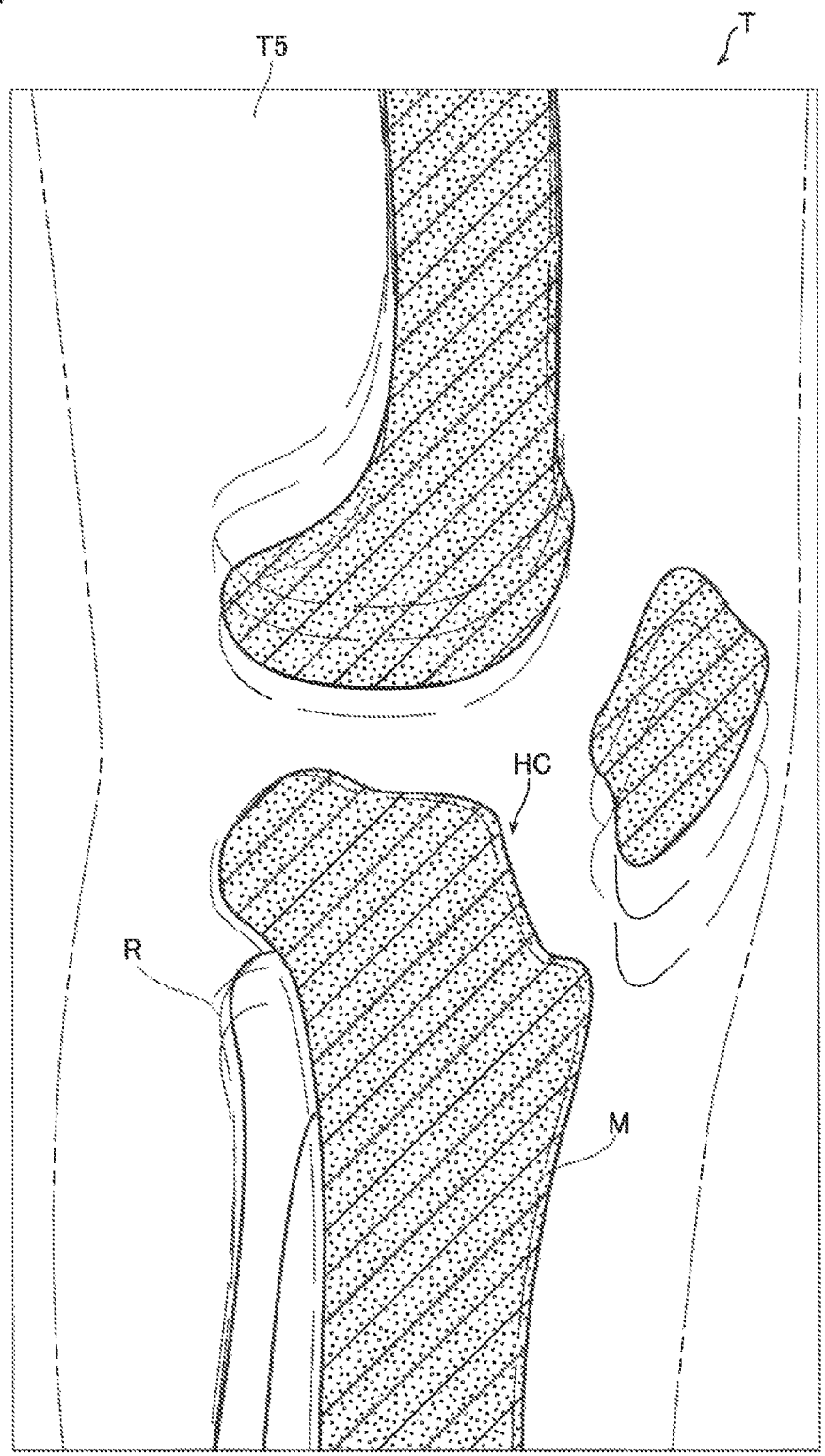
FIG. 8 is a schematic front view showing an addition tomographic image captured by the X-ray imaging apparatus according to the embodiment of the present invention.

Furthermore, as shown in FIG. 8, the image processor 3 acquires the addition tomographic image T5 by adding the third tomographic image T4 to the subtraction tomographic image T3. At this time, the image processor 3 acquires addition luminance value information included in the addition tomographic image T5. The addition luminance value information includes the luminance value information of the microstructure information M. Thus, the luminance value information of the reduced microstructure information M of the second tomographic image T2 and the luminance value information of the reduced microstructure information M of the third tomographic image T4 are offset by each other, and thus the microstructure information M of the first tomographic image T1 is clearly displayed.

That is, the image processor 3 performs processing to add the third luminance value information included in the third tomographic image T4 in which the microstructure information M and the ripple artifacts R have been reduced to the subtraction luminance value information included in the subtraction tomographic image T3 including the microstructure information M. Thus, the image processor 3 can generate the addition tomographic image T5, in which the ripple artifacts R have been reduced, including the microstructure information M and image information of low-contrast regions.

<Flowchart of Tomographic Image Generation Processing>

A flowchart of tomographic image generation processing by the image processor 3 according to this embodiment is now described with reference to FIG. 9. Each step of the flowchart is performed by the image processor 3.

As shown in FIG. 9, first, in step S1, the X-ray irradiator 18 irradiates the subject 12 with X-rays at a plurality of different angles. In step S2, the image processor 3 acquires a plurality of X-ray images including the microstructure information M by the image receiver 19. In step S3, the image processor 3 reconstructs a plurality of X-ray images that have not undergone image processing to acquire the first tomographic image T1 including the microstructure information M and the first ripple artifacts R1. In step S4, the image processor 3 acquires the first luminance value information of the first tomographic image T1.

In step S5, the image processor 3 performs the first blurring processing on each of the plurality of X-ray images. In step S6, the image processor 3 reconstructs the plurality of X-ray images that have undergone the first blurring processing to acquire the second tomographic image T2 including the second ripple artifacts R2. In step S7, the image processor 3 acquires the second luminance value information of the second tomographic image T2.

In step S8, the image processor 3 performs the second blurring processing on each of the plurality of X-ray images. In step S9, the image processor 3 reconstructs the plurality of X-ray images that have undergone the second blurring processing to acquire the third tomographic image T4 in which the microstructure information M and the ripple artifacts R have been reduced. In step S10, the image processor 3 acquires the third luminance value information of the third tomographic image T4.

In step S11, the image processor 3 subtracts the second luminance value information from the first luminance value information to acquire the subtraction luminance value information. In step S12, the image processor 3 acquires the subtraction tomographic image T3 including the subtraction luminance value information. In step S13, the image processor 3 adds the third luminance value information to the subtraction luminance value information to acquire the addition luminance value information. In step S14, the image processor 3 acquires the addition tomographic image T5 including the addition luminance value information. Then, the addition tomographic image T5 is displayed on the display 16, and the tomographic image generation processing is terminated.

Advantages of This Embodiment

In this embodiment, the following advantages are obtained.

In this embodiment, as described above, the image processor 3 is configured to acquire the first tomographic image T1 including the microstructure information M and the first ripple artifacts R1 and the second tomographic image T2 including the second ripple artifacts R2 based on the plurality of X-ray images and to acquire the subtraction tomographic image T3 by subtracting the second tomographic image T2 from the first tomographic image T1. In the second tomographic image T2, the ripple artifacts R due to the high-contrast regions HC are acquired by blurring the regions other than the high-contrast regions HC. Thus, the second ripple artifacts R2 of the second tomographic image T2 are subtracted from the first ripple artifacts R1 of the first tomographic image T1 such that the ripple artifacts R due to the high-contrast regions can be reduced in the subtraction tomographic image T3. Consequently, even with a small number of X-ray images, it is possible to reliably acquire the subtraction tomographic image T3 in which a reduction in the image quality caused by the ripple artifacts R due to the high-contrast regions HC is significantly reduced or prevented.

In this embodiment, as described above, the image processor 3 is configured to acquire the subtraction tomographic image T3 including the differences between the first ripple artifacts R1 and the second ripple artifacts R2 and the microstructure information M by subtracting the second tomographic image T2 from the first tomographic image T1. Accordingly, the first ripple artifacts R1, which are unnecessary information, are reduced by the second ripple artifacts R2 while the microstructure information M, which is necessary information, remains, and thus the subtraction tomographic image T3 in which a reduction in the image quality caused by the ripple artifacts is significantly reduced or prevented and the necessary information remains can be acquired.

In this embodiment, as described above, the image processor 3 is configured to acquire the third tomographic image T4 by reconstructing the plurality of X-ray images that have undergone the second blurring processing and to acquire the addition tomographic image T5 by adding the third tomographic image T4 to the subtraction tomographic image T3. In the subtraction tomographic image T3, the microstructure information M remains, and information that the first tomographic image T1 and the second tomographic image T2 have in common is reduced. On the other hand, the third tomographic image T4 has the contrast information. Therefore, the subtraction tomographic image T3 and the third tomographic image T4 are added such that the addition tomographic image T5 excluding only the artifact information and including the necessary information can be acquired.

In this embodiment, as described above, the image processor 3 is configured to acquire the addition tomographic image T5 by subtracting the second luminance value information from the first luminance value information and adding the third luminance value information. Accordingly, the addition tomographic image T5 can be acquired by calculating only the luminance value information of each of the first tomographic image T1, the second tomographic image T2, and the third tomographic image T4, and thus the addition tomographic image T5 can be acquired by a simple method.

In this embodiment, as described above, in the first blurring processing, the regions each having a higher contrast than the microstructure information M are maintained as the high-contrast regions HC, and the regions other than the regions each having a higher contrast than the microstructure information M are blurred. Accordingly, the microstructure information M can be reliably removed by the first blurring processing, and thus a reduction in the microstructure information M can be significantly reduced or prevented when the second tomographic image T2 is subtracted from the first tomographic image T1.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the shift addition method is used to generate the tomographic image T from the plurality of X-ray images in the aforementioned embodiment, the present invention is not limited to this. In the present invention, a filtered back projection method, an iterative approximation method, or the like may be used to generate a tomographic image from a plurality of X-ray images.

While the TVM filter is used in the first blurring processing performed on each of the plurality of X-ray images in the aforementioned embodiment, the present invention is not limited to this. In the present invention, a non-linear filter other than the TVM filter may be used in the first blurring processing.

While the averaging filter is used in the second blurring processing performed on each of the plurality of X-ray images in the aforementioned embodiment, the present invention is not limited to this. In the present invention, a filter other than the averaging filter may be used.

While the knee joint is shown as the subject 12 in the aforementioned embodiment, the present invention is not limited to this. In the present invention, the subject may be a part of the body other than the knee joint.

While the tomographic image T includes the ripple artifacts R in the aforementioned embodiment, the present invention is not limited to this. In the present invention, the tomographic image may include blur artifacts.

While the X-ray irradiator 18 is moved by the irradiator moving mechanism 15 automatically controlled by the controller 2 in the aforementioned embodiment, the present invention is not limited to this. In the present invention, the X-ray irradiator may be configured to be manually moved.

While the image processor 3 generates the addition tomographic image T5 and outputs the same to the display 16 in the aforementioned embodiment, the present invention is not limited to this. In the present invention, the image processor may generate a subtraction tomographic image and display the same on the display. In this case, the subtraction tomographic image may be directly displayed on the display, or a processed subtraction tomographic image may be displayed on the display after image processing (program processing for supplementing the low-contrast regions, for example) is performed by the image processor.

While the microstructure information M is image information of a so-called trabecula of a bone tissue, for example, in the aforementioned embodiment, the present invention is not limited to this. In the present invention, the microstructure information may be image information other than a trabecula (image information of a fracture, for example).

While the first ripple artifacts R1 and the second ripple artifacts R2 are substantially the same artifacts in the aforementioned embodiment, the present invention is not limited to this. In the present invention, the first ripple artifacts and the second ripple artifacts may be the same artifacts.

While the image processor 3 is configured to generate the first tomographic image T1, the second tomographic image T2, and the third tomographic image T4 from the plurality of X-ray images, generate the subtraction tomographic image T3 by subtracting the second tomographic image T2 from the first tomographic image T1, and generate the addition tomographic image T5 by adding the third tomographic image T4 to the subtraction tomographic image T3 in the aforementioned embodiment, the present invention is not limited to this. In the present invention, the image processor may be configured to generate the first tomographic image, the second tomographic image, and the third tomographic image and generate the addition tomographic image by subtracting the second tomographic image from the first tomographic image and adding the third tomographic image to the subtraction result.

While the control processing of the image processor 3 is described using a flowchart in a flow-driven manner in which the processing is performed in order along a processing flow for the convenience of illustration in the aforementioned embodiment, the present invention is not limited to this. In the present invention, the control processing of the image processor may be performed in an event-driven manner in which the processing is performed on an event basis. In this case, the processing may be performed in a complete event-driven manner or in a combination of an event-driven manner and a flow-driven manner.

While the island-type X-ray imaging apparatus is shown as an example in the aforementioned embodiment, the present invention is not limited to this. The present invention can also be applied to an X-ray imaging apparatus for rounds.

DESCRIPTION OF REFERENCE NUMERALS

1: X-ray imaging apparatus (radiographic imaging apparatus)
3: image processor
12: subject
13: imager
HC: high-contrast region
M: microstructure information
R1: first ripple artifact (first artifact information)
R2: second ripple artifact (second artifact information)
T1: first tomographic image
T2: second tomographic image
T3: subtraction tomographic image
T4: third tomographic image
T5: addition tomographic image

The invention claimed is:

1. A tomographic image generation method comprising:
acquiring a plurality of projection images including microstructure information by irradiating a subject with radiation at a plurality of different angles and detecting the radiation transmitted through the subject;
acquiring a first tomographic image including the microstructure information and first artifact information by directly reconstructing the plurality of projection images;
performing first blurring processing on each of the plurality of projection images to maintain a high-contrast region and blur a region other than the high-contrast region;
acquiring a second tomographic image including second artifact information by reconstructing the plurality of projection images that have undergone the first blurring processing; and
acquiring a subtraction tomographic image by subtracting the second tomographic image from the first tomographic image.

2. The tomographic image generation method according to claim 1, wherein the second tomographic image is subtracted from the first tomographic image to acquire the subtraction tomographic image including a difference between the first artifact information and the second artifact information and the microstructure information.

3. The tomographic image generation method according to claim 2, wherein
each of the plurality of projection images undergoes second blurring processing to apply blurring throughout the projection image;
the plurality of projection images that have undergone the second blurring processing are reconstructed to acquire a third tomographic image; and
the third tomographic image is added to the subtraction tomographic image to acquire an addition tomographic image.

4. The tomographic image generation method according to claim 3, wherein the addition tomographic image is acquired by subtracting second luminance value information included in the second tomographic image from first luminance value information included in the first tomographic image and adding third luminance value information included in the third tomographic image.

5. The tomographic image generation method according to claim 1, wherein in the first blurring processing, a region having a higher contrast than the microstructure information is maintained as the high-contrast region, and a region other than the region having the higher contrast than the microstructure information is blurred.

6. A radiographic imaging apparatus comprising:
an imager configured to irradiate a subject with radiation at a plurality of different angles, to detect the radiation transmitted through the subject, and to capture a plurality of projection images including microstructure information; and
an image processor configured to process the plurality of projection images captured by the imager; wherein
the image processor is configured to acquire a first tomographic image including the microstructure information and first artifact information by directly reconstructing the plurality of projection images, to perform first blurring processing on each of the plurality of projection images so as to maintain a high-contrast region and blur a region other than the high-contrast region, to acquire a second tomographic image including second artifact information by reconstructing the plurality of projection images that have undergone the first blurring processing, and to acquire a subtraction tomographic image by subtracting the second tomographic image from the first tomographic image.

7. The radiographic imaging apparatus according to claim 6, wherein the subtraction tomographic image includes a difference between the first artifact information and the second artifact information and the microstructure information.

8. The radiographic imaging apparatus according to claim 7, wherein the image processor is configured to perform second blurring processing on each of the plurality of projection images so as to apply blurring throughout the projection image, to acquire a third tomographic image by reconstructing the plurality of projection images that have undergone the second blurring processing, and to acquire an addition tomographic image by adding the third tomographic image to the subtraction tomographic image.

* * * * *